United States Patent [19]

Chang et al.

[11] Patent Number: 5,321,183
[45] Date of Patent: Jun. 14, 1994

[54] PROCESS FOR THE REGIOSELECTIVE CONVERSION OF AROMATICS TO PARA-DISUBSTITUTED BENZENES

[75] Inventors: Clarence D. Chang, Princeton; Paul G. Rodewald, Rocky Hill, both of N.J.

[73] Assignee: Mobil Oil Corp., Fairfax, Va.

[21] Appl. No.: 939,752

[22] Filed: Sep. 2, 1992

Related U.S. Application Data

[63] Continuation of Ser. No. 850,104 Mar. 12, 1992, abandoned and a Continuation of Ser. No. 850,105, Mar. 12, 1992, abandoned.

[51] Int. Cl.$^5$ .......................... C07C 2/00; C07C 4/00; C07C 6/00
[52] U.S. Cl. .................... 585/475; 585/467; 585/323
[58] Field of Search ............... 585/467, 475, 323, 470

[56] References Cited

U.S. PATENT DOCUMENTS

| | | | |
|---|---|---|---|
| 3,682,996 | 8/1972 | Kerr . | |
| 3,698,157 | 10/1972 | Allen et al. . | |
| 4,090,981 | 3/1978 | Rodewald | 252/455 Z |
| 4,127,616 | 11/1978 | Rodewald | 585/467 |
| 4,145,315 | 3/1979 | Rodewald . | |
| 4,283,306 | 8/1981 | Herkes . | |
| 4,465,886 | 8/1984 | Rodewald . | |
| 4,477,583 | 10/1984 | Rodewald | 502/71 |
| 4,843,057 | 6/1989 | D'Amore et al. . | |
| 4,851,604 | 7/1989 | Absil et al. . | |
| 4,891,458 | 1/1990 | Innes et al. | 585/323 |
| 4,927,979 | 5/1990 | Yamagishi et al. . | |
| 4,950,835 | 8/1990 | Wang et al. | 585/467 |
| 4,950,835 | 8/1990 | Wang et al. . | |
| 4,962,257 | 10/1990 | Absil et al. | 585/475 |
| 4,973,784 | 11/1990 | Han et al. . | |
| 5,030,787 | 7/1991 | Absil et al. | 585/475 |
| 5,053,573 | 10/1991 | Jorgensen | 585/475 |

FOREIGN PATENT DOCUMENTS 296582 12/1988 European Pat. Off. .

*Primary Examiner*—Asok Pal
*Assistant Examiner*—P. Achutamurthy
*Attorney, Agent, or Firm*—Alexander J. McKillop; Dennis P. Santini; Edward F. Kenehan, Jr.

[57] ABSTRACT

Processes for converting a wide variety of aromatic hydrocarbons, such as polyalkylaromatics, into commercially useful para-substituted aromatics such as para-xylene are disclosed. The aromatic hydrocarbon feed stream is first partially converted into toluene which is then subjected to a highly para-selective methylation process. The present invention therefore provides novel processes and catalysts for increasing the para-selectivity in the selective production of para-substituted aromatic compounds. From the description provided herein, those skilled in the art will appreciate that the catalysts and processes of the present invention provide greater para-selectivity at conversion rates unattained by previously known methods.

25 Claims, 1 Drawing Sheet

PROCESS FOR THE REGIOSELECTIVE CONVERSION OF AROMATICS TO PARA-DISUBSTITUTED BENZENES

CROSS-REFERENCE TO RELATED APPLICATION

This application is a continuation-in-part of copending U.S. patent applications Ser. Nos. 850,104, abandoned and 850,105, abandoned both filed Mar. 12, 1992.

BACKGROUND OF THE INVENTION

1. Field of the Invention

The present invention is directed to a process for the regioselective production of para-substituted compounds, e.g. para-xylene. A feedstock including aromatic hydrocarbons is converted to toluene which is subsequently converted to p-xylene.

2. Description of the Prior Art

Para-xylene is a very valuable commercial product useful in the production of polyester fibers. The catalytic production of para-xylene has received much attention in the scientific community and various methods for increasing catalyst para-selectivity have been described.

The synthesis of para-xylene is typically performed by methylation of toluene over a catalyst under conversion conditions. Examples are the reaction of toluene with methanol as described by Chen et al., J. Amer. Chem. Sec. 1979, 101, 6783, and toluene disproportionation, as described by Pines in "The Chemistry of Catalytic Hydrocarbon Conversions", Academic Press, N.Y., 1981, p. 72. Such methods typically result in the production of a mixture including para-xylene, ortho-xylene, and meta-xylene. Depending upon the para-selectivity of the catalyst and the reaction conditions, different percentages of para-xylene are obtained. The yield, i.e., the amount of feedstock actually converted to xylene, is also affected by the catalyst and the reaction conditions.

Previously known toluene methylation reactions typically provide many by-products such as those indicated in the following formula:

Thermodynamic Equilibria for Toluene Conversion to the Products Indicated

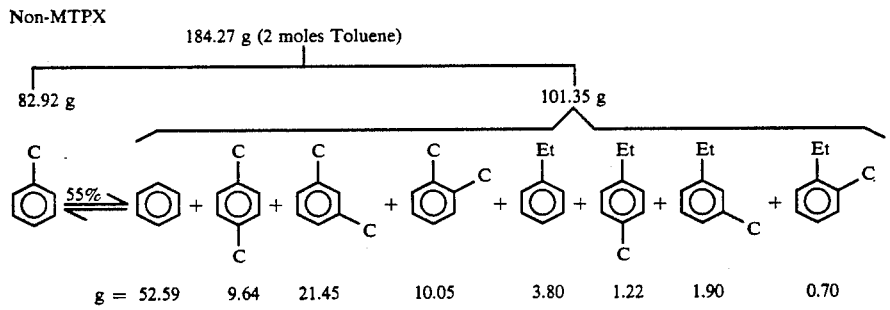

$$\text{Yield} = \text{Selectivity} \times \text{Conversion} = \frac{9.64}{101.35} \times 0.55 = 5.23 \text{ wt \%}$$

$$\text{p-Xylene Yield} = 100 \times \frac{9.64}{184.27} = 5.23 \text{ wt \%}$$

p-Xylene Purity (p-Xylene/all $C_8$'s) = 21.45 wt %

One known method for increasing para-selectivity of zeolite catalysts is to modify the catalyst by treatment with "selectivating agents". Modification methods have been suggested wherein the catalyst is modified prior to use by treatment with silicon. For example, U.S. Pat. Nos. 4,477,583 and 4,127,616 disclose methods wherein a catalyst is contacted at ambient conditions with a modifying compound such as phenylmethyl silicone in a hydrocarbon solvent or an aqueous emulsion, followed by calcination. Such modification procedures have been successful in obtaining para-selectivity, i.e., para-xylene/all xylenes, of greater than about 90% but with commercially unacceptable toluene conversions of only about 10%, resulting in a yield of not greater than about 5%, i.e., 10%×52%. Such processes also produce significant quantities of ortho-xylene and meta-xylene thereby necessitating expensive separation processes in order to separate the para-xylene from the other isomers.

Typical separation procedures comprise costly fractional crystallization and adsorptive separation of para-xylene from other xylene isomers which are customarily recycled. Xylene isomerization units are then required for additional conversion of the recycled xylene isomers into an equilibrium mixture comprising para-xylene.

Those skilled in the art appreciate that the expense of the separation process is proportional to the degree of separation required. Therefore, significant cost savings are achieved by increasing selectivity to the para-isomer while maintaining commercially acceptable conversion levels.

It is, therefore, highly desirable to provide a regioselective process for the production of para-xylene from toluene while maintaining commercially acceptable toluene conversion levels.

In addition, as discussed above, toluene conversion to xylene includes benzene as an undesirable by-product. Furthermore, the presence of benzene and other heavier aromatics in gasoline is also a problem. The composition of gasoline is coming under increasingly strict governmental regulation due to environmental concerns. Although certain aromatics such as toluene, benzene and xylene increase gasoline octane, benzene in particular is a recognized carcinogen. Other heavier aromatic components present in gasoline are believed to be associated with auto exhaust pollution and increase gasoline end point. A gasoline must have the proper volatility (i.e. vaporizing characteristics) for use in internal combustion engines.

Heavy alkyl aromatics may be converted to lower alkyl aromatics by transalkylation. U.S. Pat. No. 4,973,784 discloses the conversion of a durene (tetramethylbenzene) by-product resulting from a methanol to gasoline (MTG) conversion by contacting a durene and benzene containing feed with a catalyst having the x-ray diffraction pattern of PSH-3 or MCM-22.

It would be especially desirable to provide an efficient process for the simultaneous disposal of benzene while reducing gasoline endpoint, without causing a significant octane loss. It would be additionally advantageous to reduce benzene while providing a commercially valuable para-substituted aromatic, such as para-xylene.

SUMMARY OF THE INVENTION

The present invention is for a process for regioselective conversion of a mixture of different aromatic hydrocarbons, into commercially useful para-substituted aromatics such as para-xylene. An aromatic feedstock is first contacted with a catalytic molecular sieve under first reaction conditions suitable for the production of toluene to produce a significant amount of toluene. The toluene is then contacted with a second catalytic molecular sieve at second reaction conditions to provide a p-xylene conversion product with at least 15% xylene and with a para-substituted benzene purity of at least 90%. The second step of the invention takes advantage of the highly para-selective disproportionation processes disclosed in copending parent U.S. patent applications Ser. Nos. 850,104 and 850,105, both filed on Mar. 12, 1992, which are hereby incorporated by reference.

The present invention thus includes a sequence of reactions which is contrary to conventional practices. Conventional processes to obtain a para-substituted aromatic from a mixture of aromatics, such as a mixture of xylene isomers, would typically perform expensive separation processes to directly obtain para-xylene. The present invention takes a less direct but more efficient route by recycling by-products. A product having a high para-xylene purity is obtained at a much lower cost than would have been incurred using conventional separation steps.

DETAILED DESCRIPTION OF THE INVENTION

Figure 1:
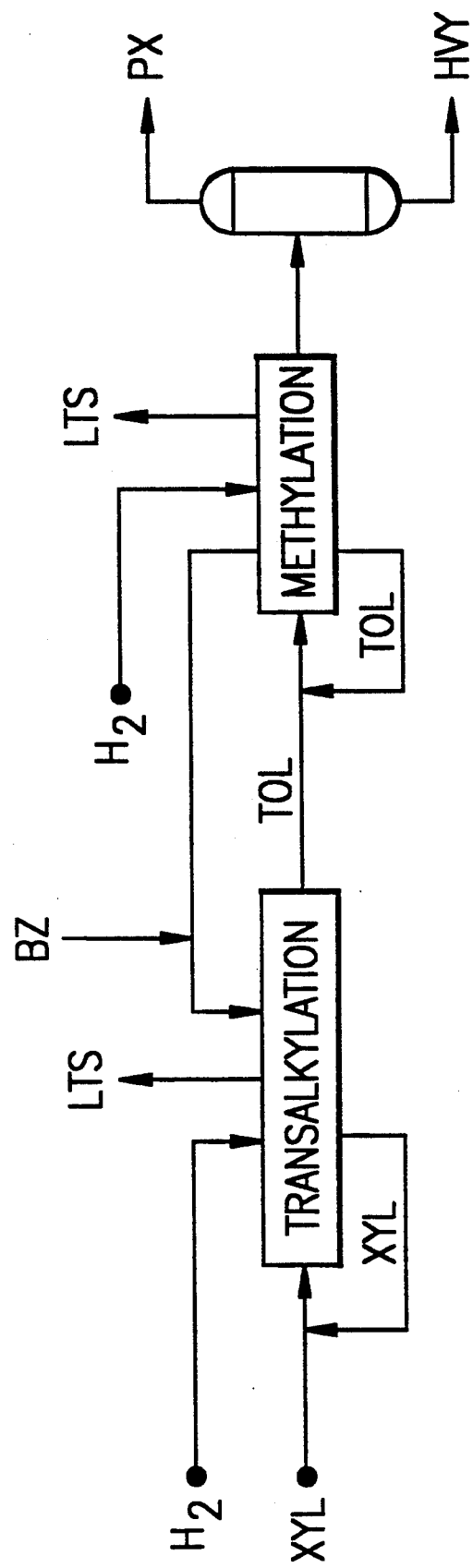
FIG. 1 schematic diagram of one embodiment of the invention.

The present invention is useful in converting various aromatics to commercially useful para-substituted benzenes, such as para-xylene, in a process involving two steps. Accordingly, polyalkylaromatics are converted to mono- and dialkylaromatics in a first step, by transalkylation with benzene over a zeolite catalyst.

Suitable zeolite catalysts for the first step include those having pores large enough to admit the polyalkylaromatics. The large pore zeolites, i.e., those zeolites having a Constraint Index less than about 1, have a pore size sufficiently large to admit the majority of polyalkylaromatics and benzene. These zeolites are generally believed to have a pore size in excess of about 7 Angstroms and are represented by zeolites having the structure of, e.g., ZSM-4, ZSM-18, ZSM-20, Zeolite Beta, mordenite, Zeolite Y, REY, Dealuminized Y (Deal Y) Ultrastable Y (USY) and Zeolite X. Also suitable are MCM-22 and PSH-3.

ZSM-4 is described in U.S. Pat. No. 3,923,639. ZSM-18 is described in U.S. Pat. No. 3,950,496. ZSM-20 is described in U.S. Pat. No. 3,972,983. Zeolite Beta is described in U.S. Pat. No. 3,308,069 and Re. No. 28,341. USY is described in U.S. Pat. Nos. 3,293,192 and 3,449,070. Deal Y is described in U.S. Pat. No. 3,442,795. REY is described in U.S. Pat. No. 4,678,765. Zeolite X is described in U.S. Pat. No. 2,882,244. MCM-22 is described in U.S. Pat. No. 4,954,325. PSH-3 is described in U.S. Pat. No. 4,439,409.

In addition, many of the intermediate pore zeolites have pores large enough to admit some aromatics. Medium pore zeolites are considered to have a Constraint Index from about 1 to about 12. Zeolites which conform to the specified values of Constraint Index for intermediate pore zeolites include ZSM-5, ZSM-11, ZSM-12, ZSM-21, ZSM-22, ZSM-23, ZSM-35, ZSM-38, ZSM-5/ZSM-11 intermediate, ZSM-48 and ZSM-50 which are described, for example, in U.S. Pat. No. 3,702,886 and Re. Nos. 29,949, 3,709,979, 3,832,449, 4,046,859, 4,556,447, 4,076,842, 4,016,245, 4,229,424, 4,397,827 and 4,640,849 to which reference is made for details of these zeolites. These zeolites may be produced with differing silica:alumina ratios ranging from 12:1 upwards. They may, in fact, be produced from reaction mixtures from which aluminum is intentionally excluded, so as to produce materials having extremely high silica:alumina ratios which, in theory at least may extend up to infinity. Silica:alumina ratios of at least 30:1 and higher will be common for these zeolites, e.g. 70:1, 200:1, 500:1, 1600:1 or even higher. Highly siliceous forms of zeolites ZSM-5, ZSM-11 and ZSM-12 are described, respectively, in U.S. Pat. No. Re. 29,948 and European Patent Publication No. 14,059 to which reference is made for details of these zeolites. Preferred intermediate pore zeolites include ZSM-5, ZSM-11, ZSM-12, ZSM-35 and ZSM-38.

Zeolites used in the first step are in the hydrogen or hydrogen precursor form, may also contain a metal component such as platinum, palladium, nickel and other metals of Periodic Table Group VIII and combinations thereof and may be incorporated with a binder as is known in the art.

Reaction conditions in the transalkylation step include temperatures ranging from about 100° C. to about 600° C., preferably from about 300° C. to about 500° C.; pressures ranging from about 0 to about 2000 psig, preferably from about 15 to about 800 psig; a mole ratio of hydrogen to hydrocarbons from about 0 (i.e. no hydrogen is present) to about 10, preferably from about 1 to about 4; at a weight hourly space velocity (WHSV) from about 0.1 to about 100 hr$^{-1}$, preferably from about 0.1 to about 10 hr$^{-1}$.

A benzene concentration is preferably maintained in stoichiometric excess relative to the polyalkylaromatics in order to maximize the conversion of polyalkylaromatics to toluene. Those skilled in the art will recognize that unconverted benzene may be recycled into the transalkylation unit.

The polyalkylaromatic feed for the first step includes aromatics of $C_6$–$C_{10}$ including as non-limiting examples, benzene, ethylbenzene, methylethylbenzene, ortho, meta, and para-xylenes and polymethylbenzenes such as durene. The skilled artisan will recognize that the choice of catalyst for the first step will depend in part on the composition of the feed to be converted.

The second step of the invention involves the methylation of toluene. The methylation reaction of the present invention is described herein in terms of disproportionation. However, the present invention also applies to other methylation reactions such as those using methylhalides and methylethers. Normally a single pass conversion of a toluene stream results in a product stream which includes dimethylbenzenes having alkyl groups at all locations, i.e., ortho-, meta-, and para-xylenes. Furthermore, the xylenes are known to proceed in a reaction which produces unwanted ethylbenzenes (EB) by the following reaction:

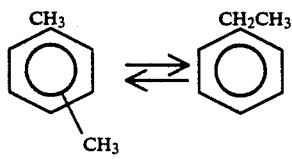

Previously, the purity of p-xylene with respect to all of the $C_8$ products in a single pass has been limited to less than 90% when isomerization is permitted. This efficiency is reduced somewhat by the production of ethylbenzene.

The present invention, however, provides high efficiency conversion which reduces production of ortho- and meta-isomers to the benefit of the desired para-isomer. The resulting product stream contains greater than a 90% purity of para-xylene. For example, the ortho-xylene isomer can be reduced to not more than about 0.5% of the total xylenes content while the meta-xylene isomer can be reduced to less than about 5% of the total xylene content. Moreover, when the reaction system is properly treated, such as by deposition of platinum on the molecular sieve, the presence of ethylbenzene can be reduced to less than about 0.3% of the $C_8$ product.

As explained in greater detail herein, the present invention provides a method for obtaining para-xylene at conversion rates of at least about 15%, preferably at least about 20-25%, and with para-xylene purity of greater than 90%, preferably at least 95%, and most preferably about 99%.

The present invention achieves higher para-xylene purity at commercially acceptable conversion rates than previously disclosed processes. The present invention thus allows for a significant reduction in process costs previously associated with the separation of unwanted by-products. Processes of the prior art typically require expensive secondary and tertiary treatment procedures in order to obtain these efficiencies.

The second step of the present invention comprises the regioselective conversion of toluene to para-xylene by methylating toluene in a reaction stream containing a toluene feed with a trim selectivated catalytic molecular sieve which may also be pre-selectivated and reaction conditions to provide a single pass, para-xylene purity of at least about 90% based on the $C_8$ products. The trim selectivation and pre-selectivation methods are described below. As used herein, the term "para-xylene purity" means the percentage of para-xylene in all of the $C_8$ products which include ethylbenzene, para-xylene, ortho-xylene, and meta-xylene. Those skilled in the art will appreciate that the proximity of the boiling points of these $C_8$ products necessitates more expensive separation processes whereas para-xylene may be more readily separated from other components in the product stream such as benzene, toluene, and para-ethyltoluene.

As used herein, the term "xylene-conversion product" indicates the total amount of xylenes resulting from the disproportionation reaction. The word "para-xylene" in this term is not intended to limit the scope of the present invention to the production of xylenes since other para-substituted aromatics may be produced.

In a preferred embodiment, the second step also comprises a method for the regioselective production of para-xylene by passing a reaction stream which contains an aromatic feedstock, e.g., toluene, in a single pass, over a trim-selectivated catalytic molecular sieve, which may also be pre-selectivated, the single pass in the presence of hydrogen at reaction conditions suitable to provide para-xylene purity of greater than about 90%. The product stream may also include small amounts of ortho- and meta-xylene and trace amounts of impurities such as ethylbenzene.

In the second step the toluene is fed simultaneously with a high-efficiency selectivating agent and hydrogen at reaction conditions until the desired p-xylene selectivity, e.g., 90% or 95%, is attained, whereupon the feed of selectivating agent is discontinued. This co-feeding of selectivating agent with toluene will be termed "trim selectivation". Reaction conditions for this trim-selectivation step generally include a temperature of about 350°-540° C. and a pressure of about atmospheric—5000 psig. The feed is provided to the system at a rate of about 0.1-20 WHSV. The hydrogen is fed at a hydrogen to hydrocarbon molar ratio of about 0.1-20.

The high efficiency para-xylene selectivating agent for trim selectivation preferably comprises a silicon containing compound discussed in greater detail below. For example, organic silicons such as phenylmethyl silicone, dimethyl silicone, and mixtures thereof are suitable. According to one preferred embodiment of the present invention, a silicone containing phenylmethylsilicon and dimethylsilicon groups in a ratio of about 1:1 is co-fed to the system, while the other components, e.g., toluene and hydrogen, are fed in the amounts set forth above. The high-efficiency para-xylene selectivating agent is fed in an amount of about 0.1%-50% of the toluene according to this preferred embodiment. Depending upon the percentage of selectivating agent used, the trim selectivation will preferably last for about 50-300 hours, most preferably less than 170 hrs.

The catalyst may be "pre-selectivated" ex situ with a high efficiency para-xylene selectivating agent, then calcined and subsequently "trim selectivated."

As used herein, the term "high efficiency, p-xylene selectivating agent" as used for both trim selectivation and pre-selectivation is used to indicate substances which will increase the para-selectivity of a catalytic molecular sieve to the stated levels while maintaining commercially acceptable toluene to xylene conversion levels. Such substances include, for example, organic silicon compounds such as phenylmethyl silicone, dimethylsilicone, and blends thereof which have been found to be suitable.

The selectivation of the catalyst is preferably performed with a silicone containing compound. An example of silicone compounds which can be used in the present invention can be characterized by the general formula:

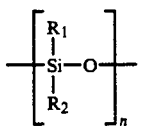

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropysilicone, polydimethylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenylcyclotrisiloxane and octaphenylcyclotetrasiloxane. Mixtures of these compounds may also be used as well as silicones with other functional groups. Other silicon-containing compounds, such as silanes, may also be utilized.

Preferably, the kinetic diameter of the high efficiency, p-xylene selectivating agent is larger than the zeolite pore diameter, in order to avoid reducing the internal activity of the catalyst.

In pre-selectivation, the silicon compound is deposited on the external surface of the catalyst by any suitable method. For example, the silicon may be dissolved in a solvent, mixed with the catalyst, and then dried. The silicon compound employed may be in the form of a solution, a liquid or a gas under the conditions of contact with a zeolite. Examples of methods of depositing silicon on the surface of the zeolite are found in U.S. Pat. Nos. 4,090,981, 4,127,616, 4,465,886 and 4,477,583 to Rodewald, which are incorporated by reference herein.

Following deposition of the silicon-containing compound in pre-selectivation, the catalyst is calcined. For example, the catalyst may be calcined in an oxygen-containing atmosphere, preferably air, at a rate of 0.2° to 5° C./minute to a temperature greater 300° C. but below a temperature at which the crystallinity of the zeolite is adversely affected. Generally, such temperature will be below 600° C. Preferably the temperature of calcination is within the approximate rang of 350° to 550° C. The product is maintained at the calcination temperature usually for 1 to 24 hours.

While not wishing to be bound by theory, it is believed that the advantages of the present invention are obtained by rendering acid sites on the external surfaces of the catalyst substantially inaccessible to reactants while 5 increasing catalyst tortuosity. Acid sites existing on the external surface of the catalyst are believed to isomerize the para-xylene exiting the catalyst pores back to an equilibrium level with the other two isomers thereby reducing the amount of para-xylene in the xylenes to only about 24%. By reducing the availability of these acid sites to the para-xylene exiting the pores of the catalyst, the relatively high level of para-xylene can be maintained. It is believed that the high-efficiency, p-xylene selectivity agents of the present invention block or otherwise render these external acid sites unavailable to the para-xylene by chemically modifying said sites.

In line with this theory, it is also believed that the presence of hydrogen in the reaction zone during the trim selectivation is important in order to maintain the desired high yields of para-xylene when a silicone compound is used as the high-efficiency para-xylene selectivating agent. The importance of the hydrogen may be reduced in alternative embodiments by using a high efficiency para-xylene selectivating agent comprising silane or some other compound which effectively renders the isomerizing acid sites on the external surface of the catalyst inaccessible.

One process of the present invention utilizes a high efficiency para-xylene selectivating agent which includes a silicon compound wherein the silicon compound is introduced by co-feeding, for example, at least one silicon compound with the toluene feedstock over a conversion catalyst at reaction conditions until the desired degree of selectivation is achieved, at which time the feed of selectivating agent may be discontinued.

The toluene feedstock preferably includes about 50% to 100% toluene, more preferably at least about 80% toluene in the toluene feedstock. Other compounds such as benzene, xylenes, and trimethylbenzene may also be present in the toluene feedstock without adversely affecting the present invention.

According to the processes of this invention, the toluene feedstock may also be dried, if desired, in a manner which will minimize moisture entering the reaction zone. Methods known in the art suitable for drying the toluene charge for the present process are numerous. These methods include percolation through any suitable dessicant, for example, silica gel, activated alumina, molecular sieves or other suitable substances, or the use of liquid charge dryers.

The catalytic molecular sieves for the second step of the present invention are in the hydrogen form and preferably comprise an intermediate pore-size zeolite such as a ZSM-5, ZSM-11, ZSM-22, ZSM-23, or ZSM-35. The catalyst preferably has an alpha value greater than 100, for example about 150–2000, and a silica-alumina ratio less than 100 preferably about 20–80. The Alpha Value of the catalyst may be increased by treating the catalyst with nitric acid or by mild steaming as discussed in U.S. Pat. No. 4,326,994. The Alpha Value is an approximate indication of the catalytic cracking activity of the catalyst compared to a standard catalyst and it gives the relative rate constant (rate of normal hexane conversion per volume of catalyst per unit time.) It is based on the activity of the amorphous silica-alumina cracking catalyst taken as an Alpha of 1 (Rate Constant $= 0.016$ sec$^{-1}$). The Alpha Test is described in U.S. Pat. No. 3,354,078 and in *The Journal of Catalysis*, Vol. 4, pp. 522–529 (August 1965): Vol. 6, p. 278 (1966); and Vol. 61, p. 395 (1980), each incorporated herein by reference as to that description. It is noted that intrinsic rate constants for many acid-catalyzed reactions are proportional to the Alpha Value for a particular crystalline silicate catalyst (see "The Active Site of Acidic Aluminosilicate Catalysts," Nature, Vol. 309, No. 5959, pp. 589-591, 14 June 1984). The experimental conditions of the test used herein include a constant temperature of 538° C. and a variable flow rate as described in detail in the *Journal of Catalysis*, Vol. 61, p. 395. The catalytic molecular sieves also preferably have a Constant Index of about 2-12. The method by which Constraint Index is determined is described fully in U.S. Pat. No. 4,016,218, incorporated herein by reference for details of the method. The crystal size of zeolites used herein is preferably greater than 0.1 micron.

For the improved disproportionation process of this invention, the suitable molecular sieve may be employed in combination with a support or binder material such as, for example, a porous inorganic oxide support or a clay binder. While the preferred binder is silica, other non-limiting examples of such binder materials include alumina, zirconia, magnesia, thoria, titanic, boria and combinations thereof, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be about 30 to about 90 percent by weight and is preferably about 50-80 percent by weight of the composition. The composition may be in the form of an extrudate, beads or fluidizable microspheres.

Operating conditions employed in the improved process of the present invention will affect the para-selectivity and toluene conversion rate. Such conditions include the temperature, pressure, space velocity, molar ratio of the reactants, and the hydrogen to hydrocarbon mole ratio. One preferred embodiment of the present invention includes contacting a catalytic molecular sieve with a toluene feed-stock which includes a silicone compound under conditions for effecting vapor-phase disproportionation. Conditions effective for accomplishing the high para-selectivity and acceptable toluene disproportionation conversion rates include a reactor inlet temperature of about 350°-540° C., preferably greater than about 400° C., a pressure of about atmospheric—5000 psig, preferably about 100 to 1000 psig, a WHSV of about 0.1-20, preferably about 2-4, and a hydrogen to hydrocarbon mole ratio of about 0.1-20, preferably about 2-4. This process may be conducted in either batch or fluid bed operation with attendant benefits of either operation readily obtainable.

The effluent is separated and distilled to remove the desired product, i.e., para-xylene, plus other by-products. The unreacted reactant, i.e. toluene, is preferably recycled for further reaction. Co-products such as benzene may be recycled to extinction (vide infra).

The catalyst may be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to about 3-4 percent. This level of ethylbenzene is unacceptable for polymer grade p-xylene since ethylbenzene in the $C_8$ product, if not removed, degrades the quality of fibers ultimately produced from the p-xylene product. Consequently, ethylbenzene content must be kept low. The specification for ethylbenzene in the $C_8$ product has been determined by industry to be less than 0.3%. Ethylbenzene can be substantially removed by isomerization or by superfractionation processes. Removal of the ethylbenzene by conventional isomerization would be impractical with the present invention since the xylene stream, which includes greater than 90% para-xylene, would be concurrently isomerized to equilibrium xylenes reducing the amount of para-xylene in this xylene stream to about 24%. It is known in the art that the alternative procedure of removing the ethylbenzene by superfractionation is extremely expensive.

In order to avoid the need for downstream ethylbenzene removal, the level of ethylbenzene by-product is advantageously reduced by incorporating a hydrogenation-dehydrogenation function in the catalyst, such as by addition of a metal compound such as platinum. While platinum is the preferred metal, other metals such as palladium, nickel, copper, cobalt, molybdenum, rhodium, ruthenium, silver, gold, mercury, osmium, iron, zinc, cadmium, and mixtures thereof may be utilized. The metal may be added by cation exchange, in amounts of about 0.01-2%, typically about 0.5%. The metal must be able to enter the pores of the catalyst in order to survive a subsequent calcination step. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The metallic compound advantageously enters the pores of the catalyst. The catalyst can then be filtered, washed with water and calcined at temperatures of about 250° to 500° C.

By the present process, toluene can be converted to aromatic concentrates of high value, e.g., about 99% para-xylene based on all $C_8$ products. In a typical embodiment of the present process, optimum toluene conversion is found to be about 20-25 weight percent with a para-xylene purity of about 90-99%.

One embodiment of the present invention comprises feeding a xylene mixture having a significant quantities of ortho-xylene, meta-xylene and para-xylene over a catalytic molecular sieve with benzene and hydrogen in a first step to form toluene. This transalkylation process is preferably performed with a stoichiometric excess of benzene in order to maximize conversion of the xylenes. Upon separation of the products of this transalkylation, the intermediate toluene stream is directed to a second step disproportionation process yielding a stream having a high purity, of the desired para-xylene in the $C_8$ fraction. Unconverted xylenes and benzene from the transalkylation process can be recycled. Similarly, a benzene product stream resulting from the disproportionation of the intermediate toluene can also be recycled as further feed for the transalkylation unit.

FIG. 1 is a schematic diagram of one embodiment of the present invention. As indicated, hydrogen, benzene (BZ) and a mixture of xylenes (XYL) are fed into a transalkylation unit to form toluene. Additional benzene may also be introduced. The products of the transalkylation unit are separated such that a light fraction (LTS) is removed, any unconverted xylenes (XYL) are recycled and a toluene stream (TOL) is fed to a methylation unit. According to this embodiment of the present invention, the toluene is co-fed along with a hydrogen feed to form a product stream having a high para-xylene (PX) purity in the $C_8$ products. The product stream is distilled to separate light hydrocarbons (LTS), remaining xylenes and toluene, leaving the heavy fraction (HVY). Any remaining toluene is recycled to the second step while benzene from the product stream is recycled back to the transalkylation unit.

The following examples will serve to further illustrate the processes and some advantages of the present invention, without unduly limiting same.

EXAMPLE 1

Transalkylation was carried out over a HZSM-5 catalyst using a 10/1 molar benzene/xylene feed. Operating conditions were 427° C., 500 psig, 2.0 WHSV, and a hydrogen to hydrocarbon molar ratio (H$_2$/HC) of 1.0. The results are shown in Table 1. Table 1 shows the product distribution obtained from the process of Example 1.

TABLE 1

| | Wt % | |
|---|---|---|
| Component | Feed | 427° C. |
| Benzene | 88.0 | 83.4 |
| Toluene | 0.0 | 9.2 |
| Xylenes | 12.0 | 7.2 |
| Trimethylbenzenes | 0.0 | 0.2 |
| | 100.0 | 100.0 |

EXAMPLE 2

Transalkylation was carried out over a HZSM-5 catalyst using a 1/1 molar benzene/xylene feed. Operating conditions were 427° C., 450 psig, 2.0 WHSV, and a hydrogen to hydrocarbon (H$_2$/HC) molar ratio of 3.5. The results are shown in Table 2 below.

EXAMPLE 3

Transalkylation was carried out over a HZSM-5 catalyst using a 1/1 molar benzene/xylene feed. Operating conditions were 450° C., 450 psig, 2.0 WHSV, and a H$_2$/HC molar ratio of 1. The results are shown in Table 2 below.

Table 2 shows the product distribution obtained from the processes of Examples 2 and 3.

TABLE 2

| | Wt % | | |
|---|---|---|---|
| Component | Feed | EX. 2 | EX. 3 |
| Benzene | 42.4 | 37.7 | 28.8 |
| Toluene | 0.0 | 23.5 | 40.0 |
| Xylenes | 57.6 | 36.6 | 27.0 |
| Trimethylbenzenes | 0.0 | 3.5 | 4.2 |
| | 100.0 | 100.0 | 100.0 |

Examples 1 to 3 are illustrative of first step of the present invention wherein transalkylation is used to decrease the percentages of benzene and xylene in a mixture to produce toluene. The data indicate that transalkylation occurs with both benzene and xylenes decreasing to produce the desired toluene and a small amount of trimethylbenzenes.

The data also indicates the reaction conditions can be varied to affect the conversion.

The toluene is readily separated from the other transalkylation products by conventional distillation in order to provide an intermediate toluene-containing stream for further conversion to p-xylene. Those skilled in the art will appreciate that the other trans-alkylation products including benzene, xylenes and trimethylbenzenes may be readily recycled for further transalkylation.

EXAMPLE 4

Toluene disproportionation was carried out in a fixed-bed reactor using 2 grams of a silica bound HZSM-5 catalyst having a silica/alumina ratio of 26, a crystal size of 0.1 micron, an Alpha Value of 731, and 1% silicone compound having a phenylmethyl silicon to dimethyl silicon ratio of 1:1 in a toluene feed. Operating conditions were 4.0 WHSV, 480° C., 500 psig, and a hydrogen/hydrocarbon ratio of 2. Table 3 summarizes toluene conversion and para-xylene selectivity as a function of time on stream during and after trim selectivation.

TABLE 3

| Time on Stream, hr | Conversion, wt % | para-Xylene in Xylenes, wt % |
|---|---|---|
| 1 | 56 | 22 |
| 6 | 57 | 21 |
| 22 | 51 | 24 |
| 46 | 42 | 39 |
| 98 | 36 | 70 |
| 143 | 28 | 86 |
| 170 | 25 | 89 |
| 174* | 25 | 91 |
| 342* | 25 | 91 |

*Silicone co-feed discontinued.

It is noteworthy that the silicone trim selectivation substantially increased para-xylene selectivity from an initial 22% to 89%. A para-xylene selectivity of 89% was achieved after 170 hours. At 174 hours on stream the feed was changed to 100% toluene, i.e., the silicone co-feed was discontinued. Over the following one week test period, toluene conversion remained constant at 25% and para-xylene selectivity remained constant at 91%.

EXAMPLE 5

Silicone trim selectivation of 2 grams of silica bound HZSM-5 was carried out as in Example 4, at 4.0 WHSV, 446° C., 500 psig, and a hydrogen/hydrocarbon ratio=2. Table 4 summarizes toluene conversion and para-xylene selectivity as a function of time on stream.

TABLE 4

| Time on Stream, hr | Conversion, wt % | p-Xylene in Xylenes, wt % |
|---|---|---|
| 1 | 44 | 29 |
| 25 | 42 | 34 |
| 47 | 37 | 58 |
| 94 | 31 | 86 |
| 143 | 29 | 93 |
| 176 | 27 | 96 |
| 199 | 26 | 97 |
| 223 | 25 | 97 |
| 239* | 25 | 97 |

*Silicone co-feed discontinued.

Silicone trim selectivation increased para-xylene selectivity from 24% (thermodynamic value) to a high 97% at 25% toluene conversion. When the silicone co-feed was discontinued, the para-xylene selectivity and toluene conversion were unchanged at 97% and 25%, respectively.

EXAMPLE 6

Silicone selectivation of 2 g of a silica bound HZSM-5 was also carried out as in Example 4, at 4.0 WHSV, 420° C., 0 psig, and hydrogen/hydrocarbon ratio=0. Table 5 summarizes toluene conversion and para-xylene selectivity as a function of time on stream. Note that the conversion drops to essentially zero at 184 hours on stream in contrast to operation in the presence of hydrogen where at 184 hours onstream conversion has stabilized at 25%.

TABLE 5

| Time on Stream, hr | Conversion, wt % | para-Xylene in Xylenes, wt % |
|---|---|---|
| 1 | 14 | 27 |
| 48 | 8 | 51 |
| 96 | 2 | 82 |
| 136 | 1 | 93 |
| 184 | 0.1 | 97 |

It was therefore determined that it was beneficial to include hydrogen in the feedstock when the high efficiency, p-xylene selectivating agent is a silicone compound. A toluene feedstock comprising 1% phenylmethyl silicone and hydrogen or nitrogen in an amount equal to a subject gas to hydrocarbon ratio of 2, was fed over the catalyst at 480° C., at a pressure of 500 Psig and at WHSV of 4. The para-selectivity of the reaction in the presence of hydrogen gas increased steadily to a level of about 90% at a toluene-to-xylene conversion of about 25%. As indicated in Table 3 (Example 4 above), the para-selectivity and conversion continued at high levels even after the feedstock was changed to 100% toluene after about 170 hours on stream. In the presence of nitrogen, on the other hand, the catalyst deactivated rapidly and conversion quickly approached zero. The results therefore indicate that the use of nitrogen with a silicone selectivating agent in the absence of hydrogen fails to provide the advantages of the present invention.

A 1% solution of silicone in toluene need not be optimal, i.e., a more rapid selectivation may occur with a 5% solution. Also, although a silicone containing phenylmethylsilicon and dimethylsilicon groups was used in this study, other silicon and organosilicon compounds may be effective in increasing the para-selectivity of the disproportionation reaction.

EXAMPLE 7

A silica modified HZSM-5 was pre-selectivated by adding 5.00 g HZSM-5 to 1.26 g phenylmethylpolysiloxane dissolved in 40 cc hexane. The solvent was distilled and the catalyst was air calcined at 1° C./min to 538° C. then 6 hours at 538° C. The catalyst contained a nominal 10% added silica.

Silicone trim selectivation of the 10% $SiO_2$-HZSM-5 was carried out as in Example 4, at 446° C., 500 psig, 4.0 WHSV, and hydrogen/hydrocarbon ratio=2. Table 6 shows toluene conversion and para-xylene selectivity for 10% $SiO_2$-HZSM-5 as a function of time on stream.

TABLE 6

| Silicone Selectivation of 10% $SiO_2$-HZSM-5 | | |
|---|---|---|
| Time on Stream, hr | Conversion, wt % | Para-xylene in Xylenes, wt % |
| 2 | 25 | 33 |
| 4 | 24 | 43 |
| 6 | 23 | 72 |
| 8 | 21 | 84 |
| 10 | 21 | 89 |
| 15 | 19 | 94 |
| 20 | 18 | 96 |
| 28 | 18 | 98 |

The silicone trim selectivation substantially increased para-xylene selectivity from 33% to 98% over 28 hours on stream. Feed was then changed to 100% toluene. Over the next ten hours the selectivity increased to 99% at 16% conversion. To further increase conversion, the temperature was increased to 457° C. and shortly thereafter to 468° C. The conversion rose to 21%, then decreased slightly to 20% over the next 80 hours. The para-xylene selectivity increased from 99.2% to 99.6% over the same 80 hours.

Compared to the HZSM-5 at Example 4, the pre-selectivated 10% $SiO_2$-HZSM-5 catalyst showed a substantially higher trim selectivation rate. For silica-modified HZSM-5, 89% para-xylene selectivity was achieved after only 10 hours on stream (17 times faster than the 170 hours for the HZSM-5 parent). Also, the time needed to reach optimum para-selectivation, 1 day for $SiO_2$-HZSM-5 compared to 1 week for HZSM-5, was shorter despite the higher selectivation temperature for HZSM-5(480° C. vs. 446° C.).

The total phenylmethyl silicone consumption was 6.80 g of silicone per g HZSM-5 and 1.42 gram of silicone per gram of $SiO_2$-HZSM-5. Thus selectivation of $SiO_2$-HZSM-5 consumed nearly five (4.79) times less silicone than selectivation of HZSM-5 and therein shows a catalyst cost advantage.

EXAMPLE 8

Silicone trim selectivation of a pre-selectivated 5% $SiO_2$-HZSM-5 was carried out at 446° C., 500 psig, 4.0 WHSV, and hydrogen/hydrocarbon ratio=2. The 5% $SiO_2$ catalyst was more active than the 10% $SiO_2$ catalyst and was expected to produce a more active selectivated catalyst. Table 7 shows toluene conversion and para-xylene selectivity for 5% $SiO_2$-HZSM-5 as a function of time on stream.

TABLE 7

| Silicone Selectivation of 5% $SiO_2$-HZSM-5 | | |
|---|---|---|
| Time on Stream, hr | Toluene Conversion, wt % | para-xylene in Xylenes, wt % |
| 2 | 41 | 25 |
| 4 | 41 | 27 |
| 5 | 38 | 36 |
| 7 | 35 | 54 |
| 14 | 31 | 83 |
| 21 | 27 | 95 |
| 26 | 25 | 98 |

Silicone selectivation substantially increased para-xylene selectivity from 25% to 98% over 26 hours on stream. Compared to 10% $SiO_2$-HZSM-5, the 5% $SiO_2$ catalyst showed consistently higher conversion over the one day selectivation time. Feed was then changed to 100% toluene. Over the next 6 hours the selectivity increased to 99% at 24% conversion, temperature was increased to 468° C. and WHSV was decreased to 3. Conversion increased to 27%, then gradually decreased to and remained constant at 21% for 6 days (146 hours). Correspondingly, the para-xylene selectivity was initially unchanged at 99% then gradually increased to and remained constant at 99.6%–99.9% for 6 days when the run was arbitrarily terminated.

EXAMPLE 9

A 0.05% Pt-10% $SiO_2$-HZSM-5 catalyst was prepared by adding 2.50 g of the 10% $SiO_2$-HZSM-5 prepared in Example 7 to 12.5 cc 1M ammonium nitrate solution. After 1.5 hours, a solution of 0.0025 g tetraamine platinum(II)nitrate in approximately 0.5 cc water was added. After standing overnight the catalyst was filtered, washed with water, and air calcined at 5° C./min to 350° C., then 3 hours at 350° C.

Toluene disproportionation was carried out over 2.00 g of the Pt-exchanged catalyst and the SiO$_2$-HZSM-5 catalyst of Example 7 at 446° C., 500 psig, 4 WHSV, and a hydrogen/hydrocarbon mole ration of 2.0. Table 8 shows the product distribution from the platinum exchange catalyst compared to that of Pt-free silica-modified HZSM-5 from Example 7 tested under the same operating conditions. At similar toluene conversion, the ethylbenzene product was reduced by nearly a factor of 12 using the Pt-catalyst. The undesirable C$_9$+ aromatics product also was reduced by nearly a factor of 2.

TABLE 8

| Component, wt % | Pt—SiO$_2$-HZSM-5 | SiO$_2$-HZSM-5 |
|---|---|---|
| Benzene | 45.84 | 41.65 |
| Ethylbenzene | 0.05 | 0.59 |
| Xylenes | 43.12 | 55.98 |
| C$_9+$ Aromatics | 0.99 | 1.78 |
|  | 100.00 | 100.00 |
| Ethylbenzene in C$_8$, wt. | 0.10 | 1.18 |
| p-Xylene in Xylenes, wt % | 25.8 | 29.8 |
| Toluene Conversion, wt % | 35 | 34 |

EXAMPLE 10

The Pt exchanged catalyst of Example 9 and Pt-free catalyst of Example 7 were treated in situ (trim selectivated) with a 1% solution of phenylmethylpolysiloxane in toluene at 446° C., 500 psig, 4 WHSV, and a hydrogen/hydrocarbon mole ratio of 2.0. After 32 hours on stream the feed was changed to 100% toluene. Table 9 shows the product distribution compared to that of Pt-free, siloxane treated, silica-modified HZSM-5 tested under the same operating conditions.

TABLE 9

| Component, wt % | Pt—SiO$_2$-HZSM-5 | SiO$_2$-HZSM-5 |
|---|---|---|
| Benzene | 46.62 | 38.43 |
| Ethylbenzene | 0.33 | 1.18 |
| Xylenes | 52.35 | 58.56 |
| C$_9+$ Aromatics | 0.70 | 1.83 |
|  | 100.0 | 100.00 |
| Ethylbenzene in C$_8$, wt % | 0.63 | 1.98 |
| p-Xylene in Xylenes, wt % | 98.4 | 98.7 |
| Toluene Conversion, wt % | 25 | 22 |

At similar toluene conversion, the ethylbenzene product was reduced by a factor of 3.6 using the Pt-catalyst while the p-xylene selectivities remained very high at 98.4%–98.7%. The undesirable C$_9$+ aromatics product was also reduced by nearly a factor of 3.

The results of Examples 11, 12 and 13 below, which are reported in Table 10 below, indicate the beneficial effect on ethyl-benzene in the product stream by the addition of platinum to the catalytic molecular sieve.

EXAMPLE 11

Silicone trim selectivation of a 10% SiO$_2$-HZSM-5 was carried out using 1% phenylmethyl silicone in a toluene feed at 446° C., 500 psig, 4.0 WHSV, and a hydrogen/hydrocarbon ratio=2. At 31 hours on stream the feed was changed to 100% toluene. At 52 hours on stream the temperature was increased to 468° C. and at 165 hours the WHSV was lowered to 3.0. The data at 39 days on stream are shown in column 1 of Table 10.

EXAMPLE 12

Silicone trim selectivation of a 0.025%Pt 10%SiO$_2$-HZSM-5 was carried out using 1% phenylmethyl silicone in a toluene feed at 446° C., 500 psig, 4.0 WHSV, and a hydrogen/hydrocarbon ratio=2. At 56 hours on stream the feed was changed to 100% toluene. At 73 hours on stream the temperature was increased to 468° C. The data at 7 days on stream are shown in column 2 of Table 10.

EXAMPLE 13

Silicone trim selectivation of a nitric acid activated 0.05% Pt 10% SiO$_2$-HZSM-5 was carried out using 1% phenylmethyl silicone in a toluene feed at 446° C., 500 psig, 4.0 WHSV, and a hydrogen/hydrocarbon ratio=2. At 27 hours on stream the feed was changed to 100% toluene. Temperature, WHSV, and hydrogen/hydrocarbon ratio were varied during the run. The data at 13 days on stream are shown in column 3 of Table 11.

TABLE

|  | Silicone | Silicone/Pt | |
|---|---|---|---|
|  | Ex. 11 | Ex. 12 | Ex. 13 |
| Reaction Conditions |  |  |  |
| Temperature, °C | 468 | 468 | 431 |
| Pressure, psig | 500 | 500 | 500 |
| H$_2$/HC | 2 | 2 | 8 |
| WHSV | 3 | 4 | 4 |
| Time on Stream, days | 39 | 7 | 13 |
| Toluene Conversion, wt % | 23 | 20 | 21 |
| Products, wt % |  |  |  |
| C$_5$ | 2.5 | 2.5 | 2.5 |
| Benzene | 43.0 | 43.6 | 47.2 |
| Ethylbenzene | 1.9 | 0.2 | 0.1 |
| Xylenes | 50.4 | 53.1 | 50.0 |
| Ethyltoluenes | 1.9 | 0.5 | 0.2 |
| C$_{10}$+ | 0.3 | 0.1 | 0.0 |
|  | 100.0 | 100.0 | 100.0 |
| p-Xylene | 99.7 | 98.7 | 99.7 |
| m-Xylene | 0.3 | 1.3 | 0.3 |
| o-Xylene | tr. | tr. | tr. |
|  | 100.0 | 100.0 | 100.0 |
| Benzene/Xylenes, m/m | 1.2 | 1.1 | 1.3 |
| p-Xylene Purity, wt % | 97.8 | 98.3 | 99.5 |

Examples 11 through 13 indicate that the levels of ethylbenzene in the reaction products of the present invention can be reduced by using a catalytic molecular sieve with a hydrogenation/dehydrogenation function such as platinum incorporated into the catalytic molecular sieve. The level of ethylbenzene in the product stream is preferably at a commercially acceptable level of not greater than 0.3%, and is most preferably not greater than about 0.2%.

As stated above, the present invention advantageously provides a product stream having a high para-xylene purity with respect to the other C$_8$ products. Table 11 provides the relative proportions of para-xylene to various combinations of other products.

TABLE 11

Comparison of Product Parameters
CATALYST

| Equilibrium Parameter | Silicone Ex. 11 | Silicone/Pt Ex. 12 | Silicone/Pt Ex. 13 | Calculated Value |
|---|---|---|---|---|
| p-Xylene/EB | 26.4 | 262 | 498 | 2.5 |
| p-Xyl/EB + m,o-xyl (other C$_8$) | 23.9 | 58.2 | 166 | 2.5 |
| p-Xyl/EB + m,o-Xyl + C$_9$ | 12.6 | 37.4 | 99.6 | 1.6 |

TABLE 11-continued

Comparison of Product Parameters

| Equilibrium Parameter | CATALYST | | | Calculated Value |
|---|---|---|---|---|
| | Silicone Ex. 11 | Silicone/Pt Ex. 12 | Ex. 13 | |
| (other C$_8$ + C$_9$) | | | | |
| p-Xylene purity (in all C$_8$s), wt % | 95.7 | 98.3 | 99.5 | 71.8 |
| p-Xylene yield (based on all products and toluene), wt % | 10.6 | 10.6 | 10.2 | 11.9 |

Aging studies were also carried out using the present invention. Results showed that the high para-selectivity and conversion rates of the present invention are achieved even at about 1000 hours on stream.

The spent catalyst can be regenerated by methods known in the art, such as by air regeneration. Thereafter, the catalyst can once again be trim selectivated and reused.

The present invention therefore provides novel processes and catalysts for increasing the para-selectivity in the selective production of para-substituted aromatic compounds. From the description provided herein, those skilled in the art will appreciate that the catalysts and processes of the present invention provide greater para-selectivity at conversion rates unattained by previously known methods.

What is claimed is:

1. A process for the regioselective conversion of a C$_{6-10}$ mononuclear aromatic hydrocarbon mixture to para-xylene comprising the steps of:
   (i) contacting said aromatic mixture with a first catalytic molecular sieve at first reaction conditions suitable for transalkylating a portion of said aromatic mixture to toluene in a first reaction to form an intermediate product stream containing toluene; and
   (ii) disproportionating by contacting said toluene with a second catalytic molecular sieve, at second reaction conditions suitable to provide a p-xylene conversion product with a para-substituted benzene purity of at least about 90% with a toluene conversion of at least about 15%.

2. The process of claim 1 wherein said second molecular sieve is treated with a silicon containing compound at reaction conditions suitable for converting toluene to xylene.

3. The process of claim 2 wherein said second molecular sieve is treated with hydrogen simultaneously with said silicon containing compound.

4. The process of claim 2 wherein the second contacting step (ii) comprises contacting a reaction stream comprising at least 80% toluene and at least 0 1% silicone compound with said catalytic molecular sieve.

5. The process of claim 4 wherein the silicone compound comprises a phenyl-substituted silicone.

6. The process of claim 1 further comprising the step of pre-selectivating said second catalytic molecular sieve with a silicon-containing compound prior to the second contacting step (ii).

7. The process of claim 6 wherein said pre-selectivation comprises contacting said second molecular sieve with said silicon-containing compound and calcining.

8. The process of claim 1 wherein said second catalytic molecular sieve comprises a Constraint Index of about 1 to about 12, and said second reaction conditions comprise a temperature of about 350° to 540° C., a pressure of about atmospheric to 5000 psig, a WHSV of about 0.1 to 20 hours$^{-1}$, and a hydrogen to hydrocarbon molar ratio of about 0.1 to 20.

9. The process of claim 1 wherein said second catalytic molecular sieve comprises a silica-bound ZSM-5 with a crystal size of at least about 0.1 micron.

10. The process of claim 1 wherein the second contacting step (ii) provides a conversion product comprising at least 20% xylene with a para-xylene purity of at least 95%.

11. A process of claim 1 further comprising the steps of providing said first and second catalytic molecular sieves with a metal hydrogenation-dehydrogenation function.

12. The process of claim 11 wherein said metal comprises platinum.

13. The process of claim 1 wherein the second contacting step (ii) provides a p-xylene conversion product comprising not more than 1% ortho-xylene, and not more than 9% meta-xylene.

14. The process of claim 1 wherein the first reaction conditions in the first contacting step (i) comprise a temperature of from about 100° C. to about 600° C., pressure from about 0 to about 2000 psig, a hydrogen to hydrocarbon mole ratio of from about 0 to about 10, and a WHSV from about 0.1 to about 100 hr$^{-1}$.

15. The process of claim 1 wherein the first catalytic molecular sieve comprises a constraint index greater than 0 and less than about 12.

16. The process of claim 1 wherein the aromatic mixture comprises aromatics selected from the group consisting of benzene, ethylbenzene, methylethylbenzene, ortho-xylene, meta-xylene, para-xylene, trimethylbenzene, tetramethylbenzene and mixtures thereof.

17. The process of claim 16 wherein the aromatic mixture comprises a stoichiometric excess of benzene relative to other aromatics.

18. The process of claim 1 further comprising the step of separating said toluene from said intermediate product stream prior to contacting said toluene with said second catalytic molecular sieve.

19. The process of claim 1 further comprising a step of recycling at least some of the intermediate product stream into said first reaction.

20. The process of claim 1 wherein said second contacting step (ii) also produces benzene and wherein said benzene is recycled into said first reaction.

21. A process for the regioselective conversion of a mixture of isomeric xylenes to para-xylene comprising:
   (i) transalkylating a mixture of isomeric xylenes with benzene in the presence of a first molecular sieve catalyst to form a product mixture containing toluene; and
   (ii) disproportionating the toluene in the presence of a second molecular sieve catalyst under reaction conditions providing a conversion product comprising at least 20 percent xylene with a para-xylene purity of at least 90 percent.

22. A process of claim 21 further comprising the steps of providing said first and second catalysts with a metal hydrogenation-dehydrogenation function.

23. The process of claim 21 further comprising the step of pre-selectivating said second catalyst with a silicon-containing compound prior to the second contacting step (ii).

24. The process of claim 21 wherein said second catalytic molecular sieve comprises a Constraint Index of about 1 to about 12, and said second reaction conditions comprise a temperature of about 350° to 540° C., a pressure of about atmospheric to 5000 psig, a WHSV of about 0.1 to 20 hours$^{-1}$, and a hydrogen to hydrocarbon molar ratio of about 0.1 to 20.

25. The process of claim 21 wherein said second catalyst is treated with a silicon containing compound at reaction conditions suitable for toluene disproportionation.

* * * * *